United States Patent [19]

Wirth et al.

[11] Patent Number: 4,778,612
[45] Date of Patent: Oct. 18, 1988

[54] BORIC ACID COMPLEXES

[75] Inventors: Hermann O. Wirth, Bensheim, Fed. Rep. of Germany; Rolf Schumacher, Marly, Switzerland; Klaus Müller, Lörrach, Fed. Rep. of Germany

[73] Assignee: Ciba-Geigy Corporation, Ardsley, N.Y.

[21] Appl. No.: 921,921

[22] Filed: Oct. 22, 1986

[30] Foreign Application Priority Data

Oct. 24, 1985 [CH] Switzerland .................. 4581/85

[51] Int. Cl.$^4$ .................................. C10M 105/78
[52] U.S. Cl. ............................ 252/42.7; 252/49.6; 252/32.7 E; 252/48.2; 556/7; 556/45; 556/51; 556/110; 556/138; 556/172
[58] Field of Search ............. 252/42.7, 49.6, 32.7 E

[56] References Cited

U.S. PATENT DOCUMENTS

| | | | |
|---|---|---|---|
| 2,795,548 | 6/1957 | Thomas et al. | 252/49.6 |
| 3,111,383 | 11/1963 | Garrett et al. | |
| 3,133,951 | 5/1964 | Nutzel | 252/49.6 |
| 4,265,664 | 5/1981 | Saischek et al. | |
| 4,336,148 | 6/1982 | Wirth et al. | 252/49.7 |
| 4,404,408 | 9/1983 | Wirth et al. | 568/680 |
| 4,410,438 | 10/1983 | Horodysky | 252/49.6 |
| 4,425,278 | 1/1984 | Wirth et al. | |
| 4,465,605 | 8/1984 | Horodysky | 252/49.6 X |
| 4,530,771 | 7/1985 | Nakano | 252/49.6 |
| 4,541,941 | 9/1985 | Horodysky | 252/49.6 |
| 4,657,686 | 4/1987 | Holstedt | 252/49.6 |
| 4,689,162 | 8/1987 | Wirth | 252/49.6 X |

FOREIGN PATENT DOCUMENTS 0075478 9/1983 European Pat. Off. .
0125032 11/1984 European Pat. Off. .

OTHER PUBLICATIONS

Chemical Abstracts, vol. 95, (1981).

*Primary Examiner*—William R. Dixon, Jr.
*Assistant Examiner*—James M. Hunter, Jr.
*Attorney, Agent, or Firm*—Harry Falber; Edward McC. Roberts

[57] ABSTRACT

Compounds of formula I

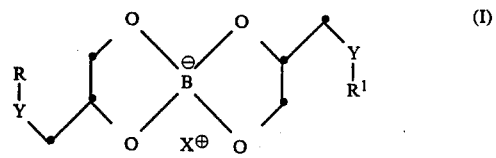

wherein R and R$^1$ are identical or different and are a radical of the formula

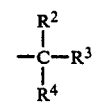

where R$^2$, R$^3$ and R$^4$ are each independently C$_1$–C$_{18}$alkyl and together contain not more than 22 carbon atoms, and R$^3$ and R$^4$ are also hydrogen, or wherein R and R$^1$ are C$_5$–C$_6$cycloalkyl, unsubstituted or C$_1$–C$_4$alkyl-substituted phenyl, or naphthyl, C$_7$–C$_{14}$aralyl, furfuryl or thienyl, and wherein Y is —S—, —O—, —NH—, —N(C$_1$–C$_{12}$alkyl)—, —CH$_2$—, —CH(C$_1$–C$_{12}$alkyl)— or —C(C$_1$–C$_{12}$alkyl)$_2$— and X$^\oplus$ is 1 equivalent of a metallic cation selected from the group consisting of Li$^\oplus$, Na$^\oplus$, K$^\oplus$, Mg$^{2\oplus}$, Ca$^{2\oplus}$, Ba$^{2\oplus}$, Zn$^{2\oplus}$, Mn$^{2\oplus}$, Ni$^{2\oplus}$, Fe$^{3\oplus}$, Fe$^{2\oplus}$, Co$^{2\oplus}$, Cu$^{2\oplus}$, Al$^{3\oplus}$, Cr$^{3\oplus}$, VO$^{3\oplus}$, ZrO$^{2\oplus}$, MoO$_2^{2\oplus}$ and TiO$^{2\oplus}$, are suitable as additives for lubricants and hydraulic oils and bring about an improvement in the extreme-pressure properties and in the anti-wear properties.

18 Claims, No Drawings

BORIC ACID COMPLEXES

The present invention relates to metal salts of complex boric acids, to the use thereof as additives in lubricants and hydraulic oils, and to lubricants and hydraulic oils containing these metal salts.

World-wide, various types of zinc dialkyldithiophosphates (ZDTP) are employed as anti-wear additives. However, in the motor oil sector there is a trend towards using anti-wear additives which are free from phosphorus or which are of low phosphorus content since it has been found that phosphorus compounds can be converted by tribofragmentation into pyro- and polyphosphates. These conversion products are most probably responsible for the inhibition of exhaust gas post-combustion catalysts. (H. S. Gandhi, W. B. Williamson and J. L. Bomback, "Deactivation of three-way and oxidation catalyst dual bed emission control systems: Catalyst post mortem analyses from methanol-fueled vehicles", Applied Catalysis, 3 (1982), pp. 79–88).

German Offenlegungsschrift specifications Nos. 2 739 312 and 2 838 473 described complexed metal salts as antistatic additives in polymers and lubricants.

The present invention relates to compounds of formula I

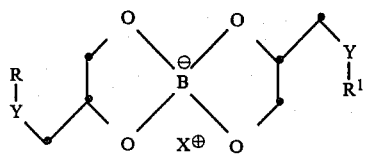

(I)

wherein R and $R^1$ are identical or different and are a radical of the formula

where $R^2$, $R^3$ and $R^4$ are each independently $C_1$–$C_{18}$alkyl and together contain not more than 22 carbon atoms, and $R^3$ and $R^4$ are also hydrogen, or wherein R and $R^1$ are $C_5$–$C_6$cycloalkyl, unsubstituted or $C_1$–$C_4$alkyl-substituted phenyl, or naphthyl, $C_7$–$C_{14}$aralkyl, furfuryl or thienyl, and wherein Y is —S—, —O—, —NH—, —N($C_1$–$C_{12}$alkyl)—, —$CH_2$—, —CH($C_1$–$C_{12}$alkyl)— or —C($C_1$–$C_{12}$alkyl)$_2$— and $X^\oplus$ is 1 equivalent of a metallic cation selected from the group consisting of $Li^\oplus$, $Na^\oplus$, $K^\oplus$, $Mg^{2\oplus}$, $Ca^{2\oplus}$, $Ba^{2\oplus}$, $Zn^{2\oplus}$, $Mn^{2\oplus}$, $Ni^{2\oplus}$, $Fe^{3\oplus}$, $Fe^{2\oplus}$, $Co^{2\oplus}$, $Cu^{2\oplus}$, $Al^{3\oplus}$, $Cr^{3\oplus}$, $VO^{3\oplus}$, $ZrO^{2\oplus}$, $MoO_2^{2\oplus}$ and $TiO^{2\oplus}$.

R and $R^1$ as a radical of the formula

are

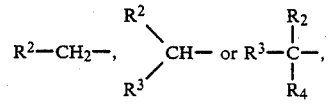

wherein $R^2$, $R^3$ and $R^4$ are each $C_1$–$C_{18}$alkyl. $R^2$, $R^3$ and $R^4$ as $C_1$–$C_{18}$alkyl are straight chain or branched substituents, for example methyl, ethyl, n-propyl, isopropyl, n-butyl, isobutyl, sec-butyl, tert-butyl, straight chain or branched pentyl, hexyl, heptyl, octyl, nonyl, decyl, undecyl, dodecyl, tridecyl, tetradecyl, pentadecyl, hexadecyl, heptadecyl or octadecyl. A preferred radical

is that wherein $R^2$, $R^3$ and $R^4$, together with the carbon atom to which they are attached, form $C_4$–$C_{20}$alkyl, with the proviso that none of these substituents $R^2$, $R^3$ and $R^4$ may be hydrogen; $C_4$–$C_{16}$alkyl is especially preferred, in particular tert-butyl, tert-nonyl or tert-dodecyl (ex Phillips Petroleum), with e.g. tert-dodecyl being understood as meaning a radical as defined for tertiary dodecylmercaptan in "Ullmanns Enzyklopädie der technischen Chemie" (Ullmann's Encyclopaedia of Industrial Chemistry), 4th Edition, Vol. 23, pp. 181–182, Verlag Chemie, Weinheim. The most preferred radical

is tert-nonyl.

R and $R^1$ as $C_5$–$C_6$cycloalkyl are cyclopentyl or cyclohexyl, preferably cyclohexyl.

If R and $R^1$ are $C_1$–$C_4$alkyl-substituted phenyl, then phenyl may be mono- to trisubstituted, preferably monosubstituted; $C_1$–$C_4$alkyl is methyl, ethyl, n-propyl, isopropyl, n-butyl, isobutyl, sec-butyl or tert-butyl.

R and $R^1$ as $C_7$–$C_{14}$aralkyl are for example benzyl, 1- or 2-phenylethyl, 3-phenylpropyl, 2-phenylisopropyl, 2-phenylhexyl, naphthylmethyl or naphthylbutyl, preferably benzyl.

R and $R^1$ are preferably identical.

If Y is a radical —N($C_1$–$C_{12}$alkyl)—, —CH($C_1$–$C_{12}$alkyl)— or —C($C_1$–$C_{12}$alkyl)$_2$—, then $C_1$–$C_{12}$alkyl moieties are straight chain or branched substituents, for example methyl, ethyl, n-propyl, isopropyl, n-butyl, isobutyl, sec-butyl, tert-butyl, straight chain or branched pentyl, hexyl, heptyl, octyl, nonyl, decyl, undecyl or dodecyl.

Y is preferably —S—, —O—, —$CH_2$—, —CH($C_1$–$C_{12}$alkyl)— or —C($C_1$–$C_{12}$alkyl)$_2$—, in particular —S—, —O— or —$CH_2$—, more particularly —S— or —O—, most preferably —S—.

$X^\oplus$ as 1 equivalent of a metallic cation is selected from the group consisting of the following cations: $Li^\oplus$, $Na^\oplus$, $K^\oplus$, $Mg^{2\oplus}$, $Ca^{2\oplus}$, $Ba^{2\oplus}$, $Zn^{2\oplus}$, $Mn^{2\oplus}$, $Ni^{2\oplus}$, $Fe^{3\oplus}$, $Fe^{2\oplus}$, $Co^{2\oplus}$, $Cu^{2\oplus}$, $Al^{3\oplus}$, $Cr^{3\oplus}$, $VO^{3\oplus}$, $ZrO^{2\oplus}$, $MoO_2^{2\oplus}$ and $TiO^{2\oplus}$, with $Li^\oplus$, $Na^\oplus$, $K^\oplus$, $Mg^{2\oplus}$, $Ca^{2\oplus}$, $Ba^{2\oplus}$, $Zn^{2\oplus}$, $Mn^{2\oplus}$, $Cu^{2\oplus}$, $VO^{3\oplus}$, $ZrO^{2\oplus}$, $MoO_2^{2\oplus}$ and $TiO^{2\oplus}$ being preferred. $Li^\oplus$, $Na^\oplus$, $K^\oplus$, $Mg^{2\oplus}$, $Ca^{2\oplus}$, $Ba^{2\oplus}$ and $Zn^{2\oplus}$ are particularly preferred.

A preferred embodiment comprises compounds of formula I, wherein R and $R^1$ are a radical of the formula

or $C_5$-$C_6$cycloalkyl, unsubstituted or $C_1$-$C_{14}$alkyl-substituted phenyl, or $C_7$-$C_{14}$aralkyl.

A particularly preferred embodiment comprises compounds of formula I, wherein R and $R^1$ are a radical of the formula

wherein $R^2$, $R^3$ and $R^4$, together with the carbon atom to which they are attached, form $C_4$-$C_{20}$alkyl, with the proviso that none of these substituents $R^2$, $R^3$ and $R^4$ may be hydrogen, or wherein R and $R^1$ are benzyl.

A more particularly preferred embodiment comprises compounds of formula I, wherein R and $R^1$ are a radical of the formula

wherein $R^2$, $R^3$ and $R^4$, together with the carbon atom to which they are attached, form $C_4$-$C_{20}$alkyl, with the proviso that none of these substituents $R^2$, $R^3$ and $R^4$ may be hydrogen.

Very interesting compounds of formula I are those wherein Y is —S—, —O—, —$CH_2$—, —CH($C_1$-$C_{12}$alkyl)— or —C($C_1$-$C_{12}$alkyl)$_2$—.

Particularly interesting compounds of formula I are those wherein Y is —S—, —O— or —$CH_2$—.

More particularly interesting compounds of formula I are those wherein Y is —S— or —O—. Especially preferred compounds of formula I are those wherein Y is —S—.

Examples of individual compounds of formula I are the following substances:

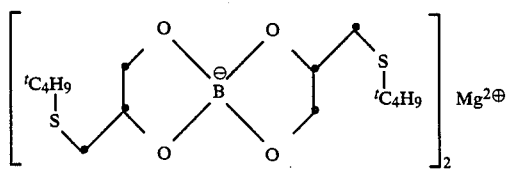

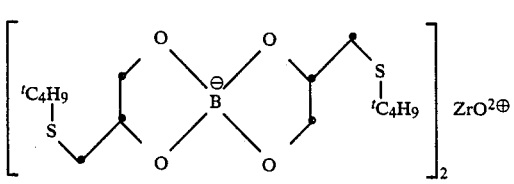

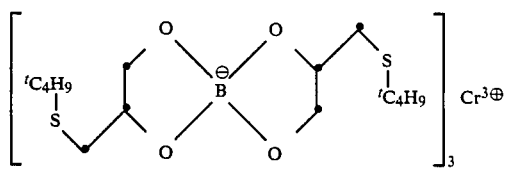

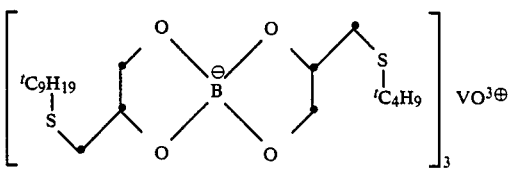

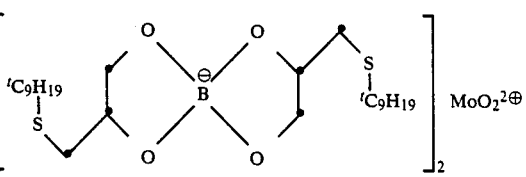

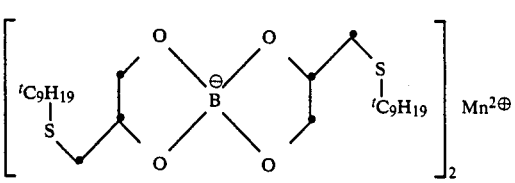

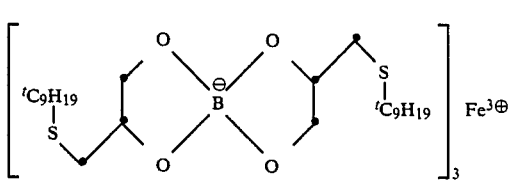

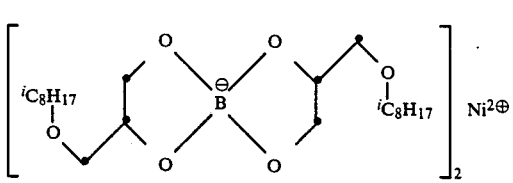

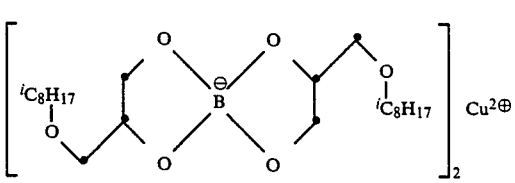

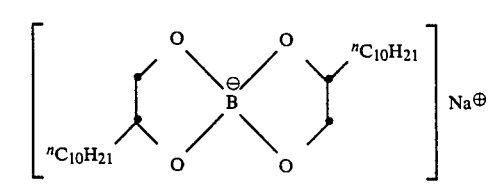

-continued

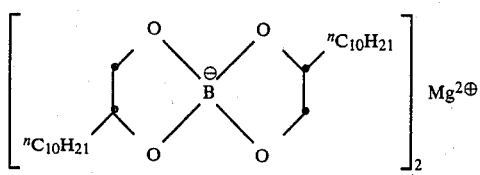

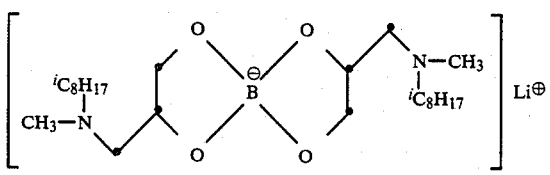

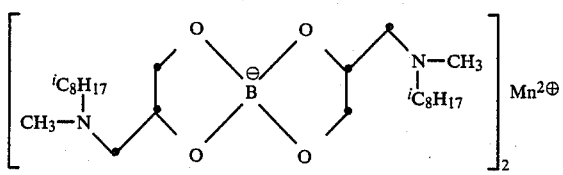

The compounds of formula I of the present invention are prepared in two stages. It is advantageous to perform both stages in the same reaction vessel.

In the first stage, an epoxide of formula II

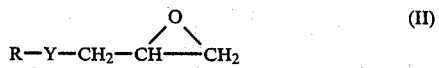
(II)

is reacted with boric acid. The reation of approximately stoichiometric amounts (2:1) is preferred. However, a slight excess of boric acid or of epoxide of formula II also produces good results.

The reaction may be carried out in a non-polar, inert solvent which is preferably water-immiscible. Examples of such solvents are chloroform, hexane, heptane, cyclohexane or toluene. The reaction can also be carried out advantageously even without a solvent, in which case the reaction medium is stirred until the boric acid has disappeared. The water of reaction is conveniently removed under reduced pressure.

The reaction temperature is not critical. The reaction is preferably carried out at elevated temperature, most preferably in the range from 80° to 150° C. It is particularly favourable to carry out the reaction at the reflux temperature of the corresponding solvent. If the reaction is carried out without a solvent, then a temperature is selected at which it is possible to remove the water of reaction under reduced pressure.

The metal salts of the present invention are prepared by reacting the product of formula III obtained in the first reaction step

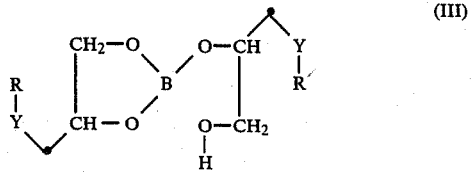
(III)

with a metal hydroxide, for example LiOH, KOH or Ba(OH)$_2$, or with a metal alcoholate, for example Mg(OR')$_2$, Ca(OR')$_2$ or Zn(OR')$_2$, e.g. in alcoholic solution or also in toluene.

For the presynthesis of the zinc alcoholate it is convenient to use the zinc dialkyl as intermediate

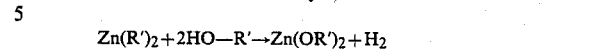

For asymmetric compounds the epoxide

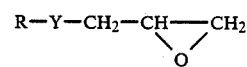

is partially replaced by

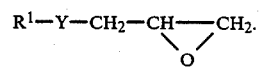

The invention further relates to compositions containing a lubricant or a hydraulic oil and an effective amount of a compound of formula I. A preferred composition is one containing a lubricant and an effective amount of a compound of formula I. A particularly preferred composition is one wherein the lubricant is a motor oil.

A further embodiment comprises a composition containing a lubricant or a hydraulic oil, in which composition the effective amount of a compound of formula I is 0.01 to 5% by weight, based on the lubricant or the hydraulic oil.

A preferred embodiment comprises a composition containing a lubricant or a hydraulic oil, in which composition the effective amount of a compound of formula I is 0.05 to 3% by weight, based on the lubricant or the hydraulic oil.

The invention also relates to the use of compounds of formula I as additives for lubricants and hydraulic oils.

The compounds of formula I are generally in a liquid state and are usually of high viscosity. They are soluble in sufficient amount in lubricants and hydraulic oils. In the case of the highly viscous representatives, dilution with e.g. a paraffin oil or also a corresponding base oil provides a favourable ready-to-use form.

The compounds of formula I are very suitable for use as additives for lubricants and hydraulic oils, in particular motor oils, and they bring about an improvement in the extreme-pressure properties and in the anti-wear properties.

Suitable lubricants are known to the person skilled in the art and are described e.g. in "Schmiermittel Taschenbuch" (Handbook of Lubricants), Hüthig Verlag, Heidelberg, 1974.

In addition to mineral oils, particularly suitable lubricants are e.g. poly-α-olefins, ester-based lubricants, and phosphates, glycols, polyglycols and polyalkylene glycols.

The lubricants may additionally contain other additives which are incorporated to enhance the basic properties of lubricants even further. These additives comprise: antioxidants, metal deactivators, rust inhibitors, viscosity index improvers, pour-point depressors, dispersants, surfactants and other extreme-pressure additives and anti-wear additives.

EXAMPLES OF PHENOLIC ANTIOXIDANTS

1. Alkylated monophenols
2,6-di-tert-butyl-4-methylphenol 2,6-di-tert-butylphenol
2-tert-butyl-4,6-dimethylphenol
2,6-di-tert-butyl-4-ethylphenol
2,6-di-tert-butyl-4-n-butylphenol
2,6-di-tert-butyl-4-isobutylphenol
2,6-dicyclopentyl-4-methylphenol
2-(α-methylcyclohexyl)-4,6-dimethylphenol
2,6-di-octadecyl-4-methylphenol
2,4,6-tricyclohexylphenol
2,6-di-tert-butyl-4-methoxymethylphenol
o-tert-butylphenol 2. Alkylated hydroquinones
2,6-di-tert-butyl-4-methoxyphenol
2,5-di-tert-butylhydroquinone
2,5-di-tert-amylhydroquinone
2,6-diphenyl-4-octadecyloxyphenol 3. Hydroxylated thiodiphenyl ethers
2,2'-thiobis(6-tert-butyl-4-methylphenol)
2,2'-thiobis(4-octylphenol)
4,4'-thiobis(6-tert-butyl-3-methylphenol)
4,4'-thiobis(6-tert-butyl-2-methylphenol)

4. Alkylidenebisphenols
2,2'-methylenebis(6-tert-butyl-4-methylphenol)
2,2'-methylenebis(6-tert-butyl-4-ethylphenol)
2,2'-methylenebis[4-methyl-6-(α-methylcyclohexyl)-phenol]
2,2'-methylenebis(4-methyl-6-cyclohexylphenol)
2,2'-methylenebis(6-nonyl-4-methylphenol)
2,2'-methylenebis(4,6-di-tert-butylphenol)
2,2'-ethylidenebis(4,6-di-tert-butylphenol)
2,2'-ethylidenebis(6-tert-butyl-4-isobutylphenol)
2,2'-methylenebis[6-(α-methylbenzyl)-4-nonylphenol]
2,2'-methylenebis[6-(α,α-dimethylbenzyl)-4-nonylphenol]
4,4'-methylenebis(2,6-di-tert-butylphenol)
4,4'-methylenebis(6-tert-butyl-2-methylphenol)
1,1-bis(5-tert-butyl-4-hydroxy-2-methylphenyl)butane
2,6-bis(3-tert-butyl-5-methyl-2-hydroxybenzyl)-4-methylphenol
1,1,3-tris(5'-tert-butyl-4'-hydroxy-2'-methylphenyl)-3-n-dodecylmercaptobutane
ethylene glycol bis[3,3-bis-(3'-tert-butyl-4'-hydroxyphenyl)butyrate]
bis(3-tert-butyl-4-hydroxy-5-methylphenyl)dicyclopentadiene
bis[2-(3'-tert-butyl-2'-hydroxy-5'-methylbenzyl)-6-tert-butyl-4-methylphenyl]terephthalate.

5. Benzyl compounds
1,3,5-tris(3,5-di-tert-butyl-4-hydroxybenzyl)-2,4,6-trimethylbenzene
bis(3,5-di-tert-butyl-4-hydroxybenzyl) sulfide
isooctyl 3,5-di-tert-butyl-4-hydroxybenzylmercaptoacetate
bis(4-tert-butyl-3-hydroxy-2,6-dimethylbenzyl) dithiolterephthalate
1,3,5-tris(3,5-di-tert-butyl-4-hydroxybenzyl) isocyanurate
1,3,5-tris(4-tert-butyl-3-hydroxy-2,6-dimethylbenzyl) isocyanurate
dioctadecyl 3,5-di-tert-butyl-4-hydroxybenzylphosphonate
calcium salt of monoethyl 3,5-di-tert-butyl-4-hydroxybenzylphosphonate.

6. Acylaminophenols
4-hydroxylauric anilide
4-hydroxystearic anilide
2,4-bis(octylmercapto)-6-(3,5-tert-butyl-4-hydroxyanilino)-s-triazine
octyl N-(3,5-di-tert-butyl-4-hydroxyphenyl)carbamate 7. Esters of β-(3,5-di-tert-butyl-4-hydroxyphenyl)propionic acid
with monohydric or polyhydric alcohols, for example with methanol, octadecanol, 1,6-hexanediol, neopentyl glycol, thiodiethylene glycol, diethylene glycol, triethylene glycol, pentaerythritol, tris(hydroxyethyl) isocyanurate, bis(hydroxyethyl)oxalyldiamide.

8. Esters of β-(5-tert-butyl-4-hydroxy-3-methylphenyl)propionic acid
with monohydric or polyhydric alcohols, for example methanol, octadecanol, 1,6-hexanediol, neopentyl glycol, thiodiethylene glycol, diethylene glycol, triethylene glycol, pentaerythritol, tris(hydroxyethyl) isocyanurate or bis(hydroxyethyl)oxalyldiamide.

9. Amides of β-(3,5-di-tert-butyl-4-hydroxyphenyl)-propionic acid, for example
N,N'-bis(3,5-di-tert-butyl-4-hydroxyphenylpropionyl)-hexamethylenediamine
N,N'-bis(3,5-di-tert-butyl-4-hydroxyphenylpropionyl)-trimethylenediamine
N,N'-bis(3,5-di-tert-butyl-4-hydroxyphenylpropionyl)-hydrazine.

EXAMPLES OF AMINE ANTIOXIDANTS

N,N'-diisopropyl-p-phenylenediamine
N,N'-di-sec-butyl-p-phenylenediamine
N,N'-bis(1,4-dimethylpentyl)-p-phenylenediamine
N,N'-bis(1-ethyl-3-methylpentyl)-p-phenylenediamine
N,N'-bis(1-methylheptyl)-p-phenylenediamine
N,N'-diphenyl-p-phenylenediamine
N,N'-di(naphthyl-2)-p-phenylenediamine
N-isopropyl-N'-phenyl-p-phenylenediamine
N-(1,3-dimethylbutyl)-N'-phenyl-p-phenylenediamine
N-(1-methylheptyl)-N'-phenyl-p-phenylenediamine
N-cyclohexyl-N'-phenyl-p-phenylenediamine
4-(p-toluenesulfonamido)diphenylamine
N,N'-dimethyl-N,N'di-sec-butyl-p-phenylenediamine
diphenylamine
4-isopropoxydiphenylamine
N-phenyl-1-naphthylamine
N-phenyl-2-naphthylamine
octylated diphenylamine
4-n-butylaminophenol
4-n-butyrylaminophenol
4-nonanoylaminophenol
4-dodecanoylaminophenol
4-octadecanoylaminophenol
bis(4-methoxyphenyl)amine
2,6-di-tert-butyl-4-dimethylaminomethylphenol
2,4-diaminodiphenylmethane
4,4'-diaminodiphenylmethane
N,N,N'N'-tetramethyl-4,4'-diaminodiphenylmethane
1,2-bis[(2-methylphenyl)amino]ethane
1,2-bis(phenylamino)propane
(o-tolyl)biguanide
bis[4-(1',3'-dimethylbutyl)phenyl]amine
tert-octylated N-phenyl-1-naphthylamine
mixture of mono- and dialkylated tert-butyl- and tert-octyldiphenylamines.

EXAMPLES OF METAL DEACTIVATORS ARE for copper, e.g.: triazole, benzotriazole and derivatives thereof, 2-mercaptobenzothiazole, 2,5-dimercaptothiadiazole, salicylidene propylenediamine, salts of salicylaminoguanidine.

EXAMPLES OF RUST INHIBITORS ARE (a) Organic acids, the esters, metal salts and anhydrides thereof, e.g.: N-oleylsarcosine, sorbitan monooleate, lead naphthenate, dodecenylsuccinic anhydride, monoalkenyl succinate, 4-nonylphenoxyacetic acid.
(b) Nitrogen-containing compounds, for example:
  I. Primary, secondary or tertiary aliphatic or cycloaliphatic amines and amine salts of organic and inorganic acids, for example oil-soluble alkylammonium carboxylates.
  II. Heterocyclic compounds, e.g. substituted imidazolines and oxazolines.
(c) Phosphorous-containing compounds, for example: amine salts of phosphoric acid partial esters.
(d) Sulfur-containing compounds, for example: barium dinonylnaphthalenesulfonates, calcium petroleum sulfonates.

EXAMPLES OF VISCOSITY INDEX IMPROVERS ARE polymethylacrylates, vinyl pyrrolidone/methacrylate copolymers, polybutene, olefin copolymers, styrene/acrylate copolymers.

EXAMPLES OF POUR-POINT DEPRESSORS ARE polymethacrylates, alkylated naphthalene derivatives.

EXAMPLES OF DISPERSANTS/SURFACTANTS ARE polybutenylsuccinimides, polybutenylphosphonic acid derivatives, basic magnesium, calcium and barium sulfonates and phenolates.

EXAMPLES OF ANTI-WEAR ADDITIVES ARE compounds which contain sulfur and/or phosphorous and/or halogen, such as sulfurised vegetable oils, zinc dialkyldithiophosphates, tritolyl phosphate, chlorinated paraffins, alkyl disulfides and aryl disulfides.

EXAMPLE 1

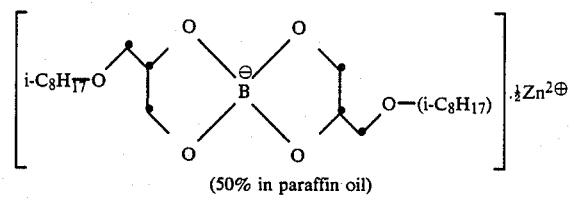

(50% in paraffin oil)

With stirring, a mixture comprising 22.4 g of 2-ethylhexyl glycidyl ether, 3.7 g of boric acid and 100 ml of toluene is heated under reflux, and the water of reaction is removed as an azeotrope. Subsequently, the mixture is cooled to 25° C., and 6.1 g of zinc di-sec-butylate are added dropwise. The mixture is then stirred for a further 30 minutes, a slight turbidity is removed by filtration, and 28.2 g of paraffin oil are added. The solvent is removed by rotary evaporation. Residue: 56.4 g of a faintly yellow viscous liquid; $n_D^{20}$: 1.4647.

EXAMPLE 2

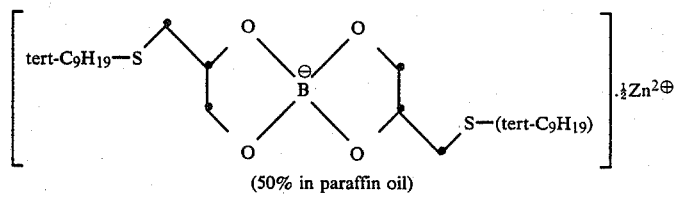

(50% in paraffin oil)

23.8 g of a boric acid ester of tert-nonyl glycerol thioether are dissolved in 100 ml of toluene and, with stirring, 5.8 g of zinc di-sec-butylate are added dropwise. The mixture is stirred for a further 30 minutes at 25° C., a slight turbidity is removed by filtration, and 26.4 g of paraffin oil are added. The toluene is subsequently distilled off by rotary evaporation. Residue: 52.8 g of a colourless liquid; $n_D^{20}$: 1.4861.

EXAMPLE 3

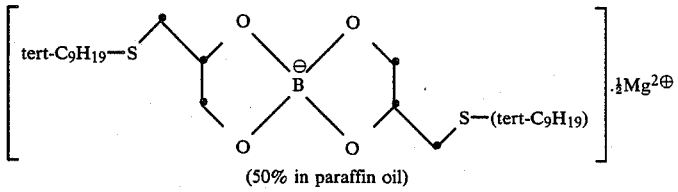

(50% in paraffin oil)

The magnesium salt is prepared in accordance with the procedure of Example 2. 1.95 g of magnesium methylate and 24.3 g of paraffin oil are employed. Residue: 48.7 g of a faintly yellow viscous liquid; $n_D^{20}$: 1.4859.

EXAMPLE 4

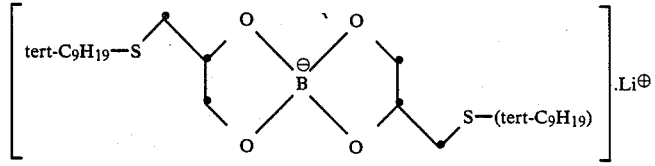

(50% in paraffin oil)

1.2 g of lithium hydroxide are dissolved in 30 ml of methanol. To the resultant solution are added 25.1 g of a boric acid ester of tert-nonyl glycerol thioether and 25.5 g of paraffin oil. The methanol is subsequently distilled off in vacuo. Residue: 51.2 g of a faintly yellow viscous liquid; $n_D^{20}$: 1.4860.

EXAMPLE 4a 3.3 g of lithium hydroxide are dissolved in 100 ml of methanol and, with stirring, 47 g of a reaction product of 2 moles of tert-butyl glycidyl thioether and 1 mole of boric acid are added to the resultant solution. When the exothermic reaction is complete, the solvent is distilled off by rotary evaporation.

Residue: 47.5 g of a vitreous solid substance; softening point: ~110° C.

EXAMPLES 5 to 8

The compounds of Examples 5 to 7 are prepared by a procedure analogous to that described in Example 4 and the compound of Example 8 is prepared by a procedure analogous to that described in Example 2. The compounds of Examples 5 to 8 are shown in Table 1 below:

Schumacher et al, ASLE Transaction 26, 1(1982), pp. 94–101).

This device is based on the following principle: a steel ball (100 Cr 6), on which a force $F_N$ acts, oscillates on a steel cylinder. The ball is fixed in a support and consequently executes an oscillating slip motion. The horizontal and vertical forces are determined by a piezoelectric force transducer. Under the test conditions selected, the maximum Hertzian normal stress was 2740 $N/mm^2$ and the maximum shear stress was 850 $N/mm^2$. The ball and cylinder were made of the same tool steel.

Several drops of oil in which the test compound had been dissolved were applied between the cylinder and the ball. The following test conditions were chosen: load: 200N, frequency: 50 Hz, amplitude: 1000μ, temperature: 100°–150° C., test duration: 2 hours.

In order to determine the wear, a cross-section was scanned with a "Talysurf" device (manufactured by the company Rank Taylor Hobson, Leicester, England). The integrated cross-sectional area served as a measure of wear.

The following compounds were tested in the ball-on-plate device:

TABLE 1

| Example | Formula | $n_D^{20}$ |
|---|---|---|
| 5 | 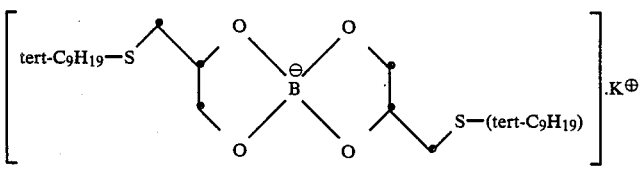 | 1.4840 |
| 6 | 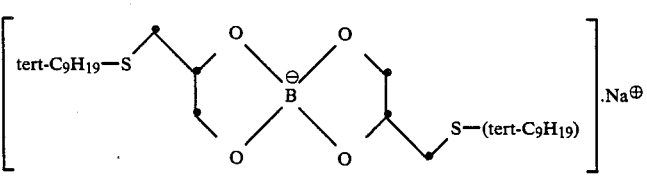 | 1.4850 |
| 7 | 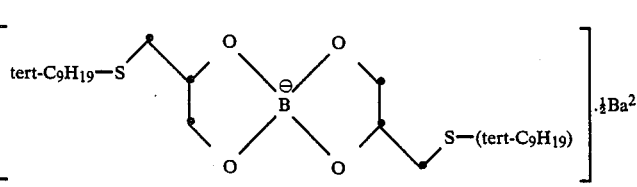 | 1.4862 |
| 8 | 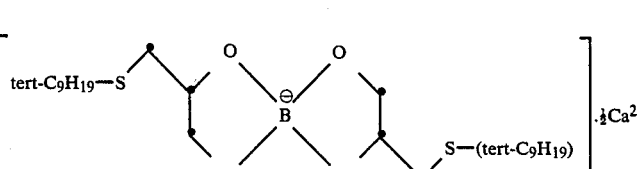 | 1.4856 |

EXAMPLE 9

Determination of the anti-wear action

The anti-wear action was determined with a commercial ball-on-plate test device (SRV equipment) manufactured by the company Optimol GmbH, Munich. (R.

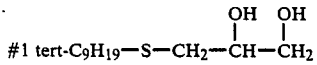
1 tert-C₉H₁₉—S—CH₂—CH(OH)—CH₂(OH)

2

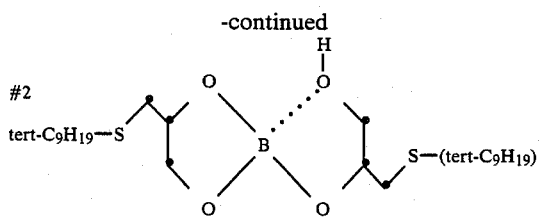

tert-C₉H₁₉—S ... S—(tert-C₉H₁₉)

3 compound of Example 5
4 compound of Example 7
5 compound of Example 2
6 compound of Example 4
7 compound of Example 8
8 compound of Example 3

9

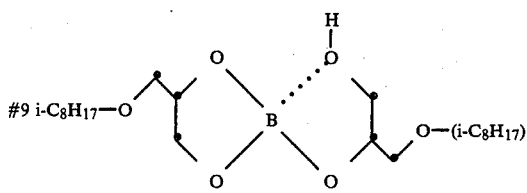

i-C₈H₁₇—O ... O—(i-C₈H₁₇)

10 compound of Example 1.

The results are shown in Table 2.

TABLE 2

| Test oil: polyalphaolefin ISO VG 100, sulfur content <1.5 ppm | | | | | |
|---|---|---|---|---|---|
| # | Conc. % by weight | Compound of Ex. | Cation | Cross-sectional area (rel. measure) | | |
| | | | | 100° C. | 120° C. | 150° C. |
| 1 | 1 | — | — | 11.5 | 14.0 | 33.8 |
| 1 | 2 | — | — | 8.7 | 27.9 | 39.1 |
| 2 | 2 | — | H⊕ | 5.3 | 6.6 | 22.5 |
| 3 | 1 | 5 | K⊕ | 6.7 | 6.8 | 10.0 |
| 4 | 2 | 7 | Ba²⊕ | 4.9 | 5.7 | 8.2 |
| 5 | 2 | 2 | Zn²⊕ | 6.8 | 6.5 | 9.7 |
| 6 | 2 | 4 | Li⊕ | 2.4 | 4.9 | 7.0 |
| 7 | 2 | 8 | Ca²⊕ | 3.2 | 4.3 | 5.1 |
| 8 | 1 | 3 | Mg²⊕ | 3.6 | 4.7 | 4.8 |
| 9 | 2 | — | H⊕ | 3.9 | 6.2 | 30.4 |
| 10 | 2 | 1 | Zn²⊕ | 4.2 | 2.3 | 7.2 |
| oil without additive | | | | 14.5 | 25 | 25 |

EXAMPLE 10

Two fully formulated 10 W/30 motor oils A+B (mineral oil, solvent-refined), each with a different zinc dialkyldithiophosphate (ZTDP) content, are tested in the manner described in Example 9.

motor oil A: ZTDP content=0.75% by weight (P content=0.055% by weight)

motor oil B: ZTDP content=1.50% by weight (P content=0.110% by weight)

2% by weight of each of the following boron compounds is added to the motor oil with a lower ZTDP content and the anti-wear properties are measured.

1

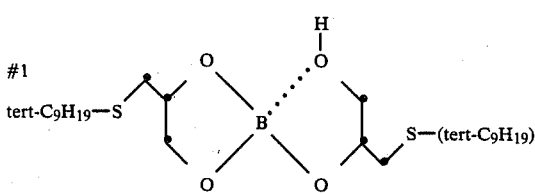

tert-C₉H₁₉—S ... S—(tert-C₉H₁₉)

2 compound of Example 5
3 compound of Example 2
4 compound of Example 4
5 compound of Example 8

6 compound of Example 3

The results are shown in Table 3.

TABLE 3

| oil | # | Conc. % by weight | Compound of Ex. | Cross-sectional area (rel. measure) | | |
|---|---|---|---|---|---|---|
| | | | | 100° C. | 120° C. | 150° C. |
| A | — | — | | 1.3 | 2.8 | 80.5 |
| B | — | — | | 1.4 | 2.2 | 5.1 |
| A | 1 | 2 | | 1.5 | 2.0 | 4.6 |
| A | 2 | 2 | 5 | 4.1 | 2.8 | 5.1 |
| A | 3 | 2 | 2 | 2.1 | 1.6 | 2.2 |
| A | 4 | 2 | 4 | 1.7 | 2.0 | 3.3 |
| A | 5 | 2 | 8 | 1.8 | 3.4 | 5.1 |
| A | 6 | 2 | 3 | 1.4 | 3.8 | 3.1 |

EXAMPLE 11

Cam and ram wear test

The test procedure is in accordance with K. Müller et al., Tribologie und Schmierungstechnik (Tribology and Lubrication Technology) 31, 3(1984), pp. 164–168.

sump lubrication: ca. 200 ml of test oil
oil temperature: 100° C.
rotational speed: 1500 rpm Test programme: The elastic force is increased every hour by 100N, beginning at 1000N peak force. The damaging force stage is reached when the total wear (cam and ram) has exceeded the value 0.25 mm.

TABLE 4

| Oil formulation | Cam and ram damaging force stage [N] |
|---|---|
| 10 W-30 motor oil (without anti-wear component) | 1100 |
| 10 W-30 motor oil + 1% of the boron compound of Ex. 4 | 1600 |
| 10 W-30 motor oil + 1.1% of Zn dialkyldithiophosphate | 1500 |
| 10 W-30 motor oil + 0.75% of Zn dialkyldithiophosphate + 0.75% of the boron compound of Ex. 4 | 2000 |
| For comparison: | |
| CEC reference oil RL 85* | 1890 (mean value of 7 individual measurements) |
| CEC reference oil RL 33* | 1320 (mean value of 5 individual measurements) |

*CEC = Coordinating European Council

The above reference oils are employed to control cam and ram wear test methods. CEC-RL 85 exhibits good behaviour; CEC-RL 33 exhibits weak behaviour.

What is claimed is:

1. A compound of the formula

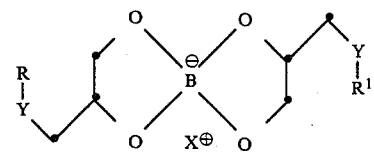

wherein
R and R¹ are identical or different and are each selected from the group consisting of C₅–C₆cycloalkyl, phenyl, C₁–C₄alkyl-phenyl, naphthyl, C₁–C₄alkyl-naphthyl, C₇–C₁₄aralkyl, furfuryl, thienyl, and a radical of the formula —C(R²)(R³)R⁴ where R², R³ and R⁴ are each independently hydrogen or C₁-C₁₈ alkyl provided that not more than two of R², R³ and R⁴ are hydrogen and that together R², R³ and R⁴ contain not more than 22 carbon atoms; Y is —S—, —O—, —NH—, —N(C₁-C₁₂alkyl)—, —CH₂—, —CH(C₁-C₁₂alkyl)— or —C(C₁-C₁₂alkyl)₂—; and X⊕ is 1 equivalent of a metallic cation selected from the group consisting of Li⊕, Na⊕, K⊕, Mg²⊕, Ca²⊕, Ba²⊕, Zn²⊕, Mn²⊕, Ni²⊕, Fe³⊕, Fe²⊕, Co²⊕, Cu²⊕, Al²⊕, Cr³⊕, VO³⊕, ZrO²⊕, MoO²⊕ and TiO²⊕.

2. A compound of claim 1, wherein R and R¹ are identical.

3. A compound of claim 1 wherein R and R¹ are a radical of the formula

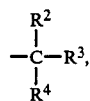

or C₅-C₆cycloalkyl, phenyl C₁-C₁₄alkyl phenyl or C₇-C₁₄aralkyl.

4. A compound of claim 1, wherein R and R¹ are a radical of the formula

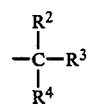

wherein R², R³ and R⁴, together with the carbon atom to which they are attached, form C₄-C₂₀alkyl, with the proviso that none of these is hydrogen, or wherein R and R¹ are each benzyl.

5. A compound of claim 4, wherein R and R¹ are a radical of the formula

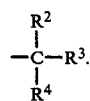

6. A compound of claim 5, wherein R and R₁ are tert-nonyl.

7. A compound of claim 1, wherein Y is —S—, —O—, —CH₂—, —CH(C₁-C₁₂alkyl)— or —C(C₁-C₁₂alkyl)₂—.

8. A compound of claim 1, wherein Y is —S—, —O— or —CH₂—.

9. A compound of claim 1, wherein Y is —S— or —O—.

10. A compound of claim 1, wherein Y is —S—.

11. A compound of claim 1, wherein X⊕ is 1 equivalent of a metallic cation selected from the group consisting of Li⊕, Na⊕, K⊕, Mg²⊕, Ca²⊕, Ba²⊕, Zn²⊕, Mn²⊕, Cu²⊕, VO³⊕, ZrO²⊕, MoO²⊕ and TiO²⊕.

12. A compound of claim 1, wherein X⊕ is 1 equivalent of a metallic cation selected from the group consisting of Li⊕, Na⊕, Mg²⊕, Ca²⊕, Ba²⊕ and Zn²⊕.

13. A composition containing a lubricant or a hydraulic oil and an amount of a compound of claim 1 sufficient to effectively improve extreme-pressure and anti-wear properties.

14. A composition according to claim 13 containing a lubricant.

15. A composition according to claim 14, wherein the lubricant is a motor oil.

16. A composition of claim 13, wherein the effective amount of the compound is 0.01 to 5% by weight, based on the lubricant or the hydraulic oil.

17. A composition of claim 16, wherein the effective amount of the compound is 0.05 to 3% by weight.

18. A process of improving the extreme pressure and anti-wear properties of a lubricant or hydraulic oil, comprising the step of adding to said lubricant or hydraulic oil an effective amount of a compound of the formula

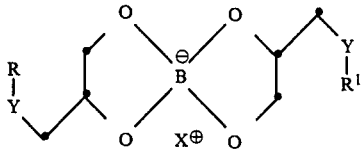

wherein
R and R¹ are identical or different and are each selected from the group consisting of C₅-C₆ cycloalkyl, phenyl, C₁-C₄alkyl-phenyl, naphthyl, C₁-C₄alkyl-naphthyl, C₇-C₁₄aralkyl, furfuryl, thienyl, and a radical of the formula —C(R²)(R³)R⁴ where R², R³ and R⁴ are each independently hydrogen or C₁-C₁₈alkyl provided that not more than two of R², R³ and R⁴ are hydrogen and that together R², R³ and R⁴ contain not more than 22 carbon atoms; Y is —S—, —O—, —NH—, —N(C₁-C₁₂alkyl)—, —CH₂—, —CH(C₁-C₁₂alkyl)— or —C(C₁-C₁₂alkyl)₂—; and
X⊕ is 1 equivalent of a metallic cation selected from the group consisting of Li⊕, Na⊕, K⊕, Mg²⊕, Ca²⊕, Ba²⊕, Zn²⊕, Mn²⊕, Ni²⊕, Fe³⊕, Fe²⊕, Co²⊕, Cu²⊕, Al²⊕, Cr³⊕, VO³⊕, ZrO²⊕, MoO²⊕ and TiO²⊕.

* * * * *